United States Patent [19]

Sandoval et al.

[11] Patent Number: 5,463,125
[45] Date of Patent: Oct. 31, 1995

[54] PHENYL ALCOHOL AMIDES HAVING ANTICONVULSANT ACTIVITY

[76] Inventors: Guillermo C. Sandoval, Cocoteros 177, Col. Neuva Santa Maria, 02800, Mexico City, Mexico; Sergio E. M. Toledo, Cerro del Fortin 110-5, Col. Campestre Churubusco, 04400-Mexico City, Mexico; Martha T. Z. Garcia, Orquidea 94, Col. Loma Linda, 52900 Naucalpan, Edo de Mexico, Mexico

[21] Appl. No.: 72,228

[22] Filed: Jun. 3, 1993

Related U.S. Application Data

[63] Continuation of Ser. No. 756,329, Sep. 6, 1991, abandoned.

[51] Int. Cl.$^6$ ................................................. C07C 233/05
[52] U.S. Cl. ........................................... 564/170; 564/161
[58] Field of Search .................................. 564/170, 161; 514/617, 622

[56] References Cited

U.S. PATENT DOCUMENTS 2,775,539  12/1956  Stoughton ............................. 514/622

FOREIGN PATENT DOCUMENTS 1668351  5/1971  Germany.
447401  12/1974  U.S.S.R. ............................... 564/170

OTHER PUBLICATIONS

Carvajal et al. Biochem Pharmacol. 13, 1059, 1964.
Perez–de–la–mora et al, Biochem. Pharmacol. 22, 2635 (1973).
Solis et al., Heurobiologia, Symp. International, 83–94, 1979.
Carvajal, Gac. Med. Mek., 3, 196 (1976).
Castellano et al, Acta Cryst., 1337, 285, 1981.
De la Cruz et al, Pharmacol. Biochem. Behav. 16, 117 (1982).
Nathan et al, Rev. Latinoamer, Quim, 9, 90 (1978).
Gallegos et al, J. of Pharmaceutical Sci, 79,(11), 1032–33, 1990.

*Primary Examiner*—Shailendra Kumar
*Attorney, Agent, or Firm*—Foley & Lardner

[57] ABSTRACT

New anticonvulsant compounds include (±)-2-hydroxy-2-phenylbutyramide and (±)-3-hydroxy-3-phenylpentamide. These homologues of (±)-4-hydroxy-4-phenylhexanamide have anticonvulsant activity as well as unexpected properties, particularly low neurotoxicity and pharmacological differences. The invention further provides methods for the synthesis of (±)-2-hydroxy-2-phenylbutyramide and (±)-3-hydroxy-3-phenylpentamide as exemplified in the examples.

1 Claim, No Drawings

PHENYL ALCOHOL AMIDES HAVING ANTICONVULSANT ACTIVITY

This is a continuation of application Ser. No. 07/756,329, filed on Sep. 6, 1991, now abandoned.

TECHNICAL FIELD

The present invention relates to anticonvulsant compounds, particularly anticonvulsant hydroxyamides, and to methods for preparation of such compounds.

BACKGROUND OF THE INVENTION

A report on the anticonvulsant activity of a series of 5,5-disubstituted-2-pyrrolidinones designed as inhibitors of γ-aminobutyric acid-α-ketoglutaric acid transaminase was published in Carvajal et al., *Biochem Pharmacol.* 13, 1059 (1964). Within this series, the 5-ethyl-5-phenyl compound showed a broad profile of anticonvulsant activity. It protects mice against seizures provoked by pentetrazol (pentylenetetrazol), maximal electroshock, and bicuculline, and cats against hippocampal kindling. See Pérez-de-la-Mora et al., *R. Biochem. Pharmacol.* 22, 2635 (1973) and Solis et al., *Neurobiologia, Symposium Internacional*, pp. 83–94, (1979). It also shows a potent clinical antiepileptic action in patients having grand mal seizures. See, Carvajal, *Gac. Méd. Méx.*, 3, 196 (1976).

Later studies using NMR spectroscopy and X-ray diffraction demonstrated that the compound which initially was thought to be 5-ethyl-5-phenylpyrrolidinone was in fact (±)-4-hydroxy-4-phenylhexanamide (compound 3 in Table 1 below). See, Joseph-Nathan et al., *Rev. Latinoamer, Quim.* 9, 90 (1978); and Castellano et al., *Acta Cryst.* B37, 285 (1981). Several studies have been made of the mechanism of action of this compound (see Perez-de-la-Mora et al. cited above, and De-La-Cruz et al., *Pharmacol. Biochem. Behav.* 16, 117 (1982)), but at present this mechanism remains unknown. A need persists to identify other hydroxyamides having useful levels of anticonvulsant activity.

SUMMARY OF THE INVENTION

Anticonvulsant compounds according to the invention include (±)-2-hydroxy-2-phenylbutyramide, also called DL-2-hydroxy-2-ethyl-2-phenyl-acetamide (DL-HEPA), and (±)-3-hydroxy-3-phenylpentamide, also called DL-3-hydroxy-3-ethyl-3-phenyl-propionamide (DL-HEPP). These homologues of (±)-4-hydroxy-4-phenylhexanamide, also called γ-hydroxy-γ-ethyl-γ-phenyl-butyramide and DL-4-hydroxy-4-ethyl-4-phenyl-butyramide (DL-HEPB), have anticonvulsant activity as well as unexpected properties, particularly low neurotoxicity and pharmacological differences as described in detail hereafter.

The invention further provides methods for the synthesis of (±)-2-hydroxy-2-phenylbutyramide and (±)-3-hydroxy-3-phenylpentamide as exemplified in the examples below. One such method for the synthesis of a hydroxyphenyl alkanamide includes the steps of (A) reacting a phenone with a cyanide salt under conditions effective to form a nitrile compound, then (B) transforming the —CN group of the nitrile compound into an —NH$_2$ group to thereby form the hydroxyphenyl alkanamide. In preferred embodiments, step (A) further comprises reacting propiophenone with a cyanide salt of the formula XCN, wherein X is a cation such as Na, whereby the end product hydroxyphenyl alkanamide is (±)-2-hydroxy-2-phenylbutyramide, or reacting propiophenone with an acetonitrile of the formula XCH$_2$CN, whereby the end product hydroxyphenyl alkanamide is (±)-3-hydroxy-3-phenylpentamide.

DETAILED DESCRIPTION

The homologous compounds (±)-2-hydroxy-2-phenylbutyramide, (±)-3-hydroxy-3-phenylpentamide and (±)-4-hydroxy-4-phenylhexanamide of the formula:

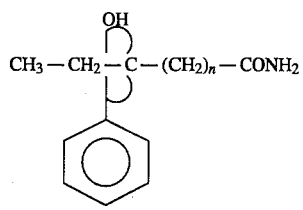

wherein n is from 0 to 2 are unrelated structurally to major known anticonvulsant drugs. In accordance with the invention, the compounds corresponding to n=0 or 1 were screened for their anticonvulsant profile and activity as compared to the known compound wherein n=2. As can be seen in Table 1 below, they show a wide spectrum of action and a generally similar profile and activity, but with certain unexpected differences. In particular, the n=0 compound had an unusually high strychnine activity, more than twice that of the n=2 compound. In the picrotoxin test, only the n=1 compound was active at a dose of 130 mg kg$^{-1}$; the other compounds showed no activity at comparable levels. This was particularly unexpected based on the homologous nature of these compounds, and shows that substantial unexpected differences in activity exist for these compounds.

In Example 4 below, a rotarod ataxia test was used to evaluate the neurotoxicity of each compound. In this test, the n=1 compound had an unusually low neurotoxicity. The different values obtained in the rotarod ataxia test between NIH results and those from the n=2 compound prepared as described below agree with the reported difference in sensitivity of the accelerating rotarod as compared with a constant speed rotarod to detect motor performance. See, Jones et al., *J. Pharm. Pharmacol.* 20, 302 (1968). Thus, the TD$_{50}$ value of 111 for the n=2 compound of Comparative Example 1 is the result to be compared to the n=0 and n=1 compounds of Examples 1 and 2. Based on the protective effect of the compounds of the invention against convulsant drugs tested, these compounds may be expected to be effective in the treatment of petit mal epilepsy.

Phenyl alcohol amide derivatives of the foregoing compounds wherein n=0 to 2 may be synthesized by substitution of the ethyl group at the center of chirality by either a methyl or phenyl group. In a preliminary test against convulsions provoked by pentylenetetrazol at a dose of 100 mg kg$^{-1}$ for test compounds, via i.p., it has been found that substitution of the ethyl group by a methyl group in the n=1 compound suppresses anticonvulsant activity, whereas the n=0 derivative retains activity and the n=2 derivative conserves half-potency. Substitution of ethyl by phenyl in the n=0 and n=1 produces a loss in anticonvulsant activity. From these results it seems that the steric volumes and lipophilicity of groups at the center of chirality are important for the anticonvulsant activity of the phenyl alcohol amides prepared.

According to a process of the invention, DL-γ-hydroxy-γ-phenyl-hexanamide or γ-hydroxy-γ-ethyl-γ-phenyl-butyraml (DL-HEPB) may be obtained by condensation of propiophenone and a succinic acid ester in the presence of a condensing agent that can be sodium, a metal, sodium hydride, or a sodium, potassium or any other adequate alkaline metal alkoxide. In this reaction the following compound (A) is obtained as a main product:

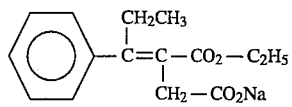

The following compound (B) is obtained with the above product:

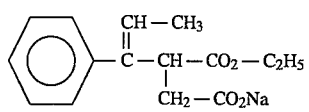

Since in the following step these products both give origin to the same lactone, it is not necessary to separate them.

These products are subjected to decarbetoxilation and lactonization. Through decarbetoxilation, the carbetoxy group is eliminated from the previously obtained compounds. Hydrochloric acid or hydrobromic acid in an acetic acid and water solution can be used to carry out this reaction. This way, a mixture of the γ derivative, disubstituted γ of vinyl-acetic acid and its corresponding lactone is obtained (γ derivative, disubstituted γ from butyrolactone).

The vinyl acetic acid derivative is separated and put through a lactonization process by which it will be transformed into the lactone. Hydrochloric or hydrobromic acid can be used to carry out this process, but in certain cases it is better to use moderately concentrated sulfuric acid. The reactions are as follows:

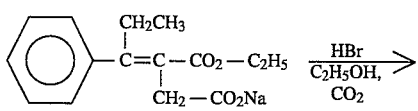

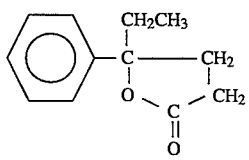

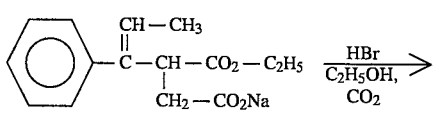

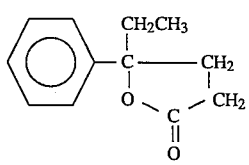

The lactone obtained in the above reactions is treated with ammonia under pressure. This way the corresponding amide (DL-5,5-disubstituted derivative from butyramide) is obtained as follows:

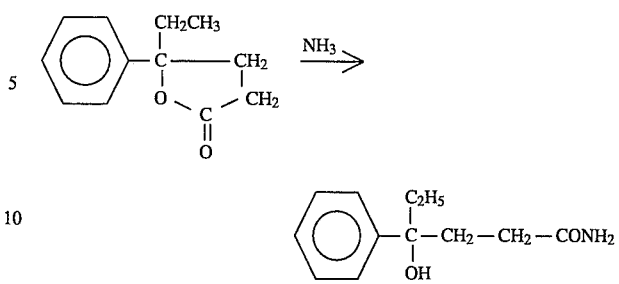

DL-4-Hydroxy-4-ethyl-4-phenyl-butyramide (DL-HEPB), the n=2 compound referred to above, may also be obtained. To obtain this compound, propiophenone is condensed with ethyl succinate using sodium hydride as a condensing agent. Other condensing agents can also be used, as for example: potassium tert-butoxide, sodium etoxide or others, but NaH is easier to handle and reacts faster. As a solvent, benzene or ether can be used, and a small amount of ethyl alcohol is added to initiate reaction. In this condensation, the compounds A and B described above are obtained in a relative amount A:B of 9 to 1.

The mixture of hemiesters obtained in the above reaction is refluxed with a hydrobromic acid solution (hydrochloric acid can be used but it is less effective), combined with acetic acid and water. During this process, the compounds undergo several transformations. First, the compounds hydrolyze. Simultaneously with hydrolysis, compound B transforms into compound A due to a migration of its double bond. This way only one type of product compound is obtained. This compound later loses the carboxyl group, turning into γ-methyl-γ-phenyl-vinyl acetic acid (1-phenyl, 3-pentoic acid).

A great amount of this acid transforms into the corresponding lactone or the γ-methyl, γ-phenyl butyrolactone. This is the product to be used in the following step. Phenylpentenoic acid is separated from the lactone and treated again with hydrobromic acid, acetic acid and water. This way practically everything transforms into lactone. The lactone obtained in these reactions is then treated with ammonia under pressure, forming DL-4-hydroxy-4-ethyl-4-phenyl-butyramide (DL-HEPB) by a ring-opening reaction in the same manner as described above.

The compounds of the invention are suitable for human or animal administration in dosage forms and amounts which can be readily determined by those skilled in the art. For this purpose, the compound of the invention is compounded with a compatible, pharmacologically acceptable carrier for administration by injection or the like.

This and other aspects of the invention are illustrated in the following examples. In the examples, melting points were determined with a Mettler apparatus and are reported uncorrected. Infrared spectra were obtained with a Perkin Elmer 1310 spectrophotometer. $^1$H-NMR spectra were determined with a Varian EM 390 spectrometer and are reported as δ (ppm) values in $CDCl_3$ with TMS as the internal standard. Elemental analysis was performed by Galbraith Laboratories, Inc., Knoxville, Tenn. (USA) and were within ±0.4% of the theoretical values.

EXAMPLE 1

Preparation of DL-2-Hydroxy-2-Ethyl-2-Phenyl-Acetamide (DL-HEPA)

In a 1000 ml, two-opening ball matrass equipped with a separating funnel and a thermometer, 89.9 grams (0.67 moles) propiophenone, 100 ml water and 80 ml ethyl ether were added. The matrass was immersed in an ice and salt bath and 82 grams (1.67 moles) granulated sodium cyanide was added. The mixture was shaken vigorously for 20 minutes, and when the mixture temperature had dropped to 5° C., 140 ml (1.7 moles) concentrated hydrochloric acid from the separating funnel was added at such a speed that the temperature of the reaction stayed between 5° C. and 10° C. The addition took nearly two hours.

The mixture was then shaken for 10 more minutes, then removed from the ice bath and shaken (stirred) for three hours at room temperature. The mixture was let stand, and the liquid part was decanted into a one liter separating funnel to separate the ether phase. The aqueous phase was poured back into the reaction matrass and 100 ml water was added to dissolve the salts.

The aqueous solution was extracted with four 50 ml portions of ether, and the initially separated ethereal phase was put back with the ether extracts in a 500 ml matrass. Ether was then distilled in a rotating evaporator and 160 ml of cold hydrochloric acid (concentrated) was added to the residue. Later, the mixture was saturated with hydrogen chloride while keeping the temperature between 10° and 15° C., then allowed to stand at room temperature for 48 hours. Excess hydrogen chloride was eliminated by bubbling air into the solution for three hours.

The solid formed was separated by means of filtration and washed with cold benzene. This solid is the DL-HEPA that crystallizes from benzene. This solid is the DL-HEPA that crystallizes from benzene. DL-HEPA is soluble in ethyl alcohol, chloroform and hot benzene and insoluble in cold benzene or water. Fusion point was 91°–92° C. Yield was 20%. The infrared spectrum of DL-HEPA shows the following maximums: 756 cm-1 (—CaH5); 2294 and 1450 cm-1 (—CH3); 3400 cm-1 (—OH); 1122 cm-1- (—C—O); 3200 cm-1 (—NH—); 1665 cm-1 (—C—O); 2880 and 2950 cm-1 (—CH$_2$—). The nuclear magnetic resonance spectrum of DL-HEPA shows the following values: $^1$H NMR (CDCL$_3$); ppm 0.92 (t,3tl,—CH$_3$); 2.11 (m, 2H,—CH$_2$—); 3.32 (S,1H,—OH); 5.85 (bs,1H,—NH—); 6.43 (bs,1H, —NH—); 7.3 (m,3H, H Phenyl); 7.58 (m, 2H, H Phenyl).

EXAMPLE 2

Preparation of DL-3-Hydroxy-3-Ethyl-3-Phenyl-Propionamide (DL-HEPP).

This synthesis required the following steps:

A. Preparation of sodamide (NaNH$_2$).

B. Preparation of DL-3-Hydroxy-3-Ethyl-3-Phenyl-Propionitrile (DL-HEPPN).

C. Preparation of DL-3-Hydroxy-3-Ethyl-3-Phenyl-Propionamide (DL-HEPP).

The reactions conducted below were:

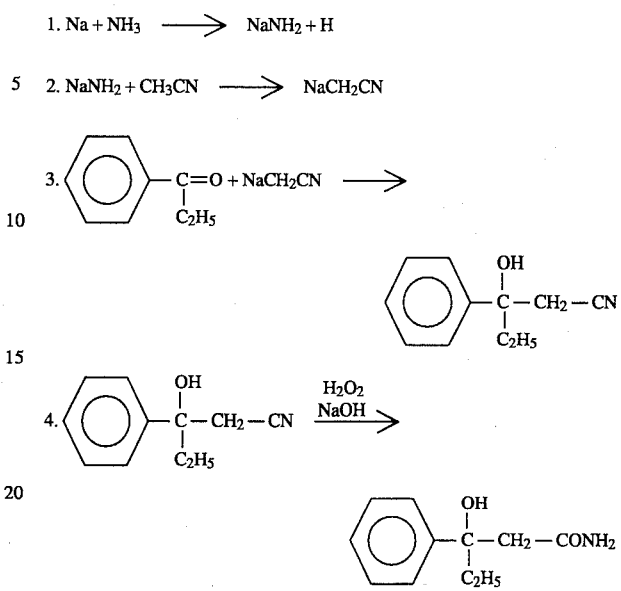

A. Preparation of Sodamide

In a 1000 ml, two neck matrass equipped with a magnetic shaker and a cooling, polished glass cap connected to a gas and soda lime absorption trap, 300 ml ammonium hydroxide (NH$_3$OH) was added. The matrass had been previously cooled off with dry ice and acetone to −80° C. Separately, metallic sodium was cut into 1.27 gm (0.05 moles) small strips and kept under petroleum. The dry ice bath was removed, and hydrated ferric nitrate crystals (approx. 0.2 gm) were added. A sodium cube (approx. 5 mm.) was cut, dried with filter paper, and added to the ammonium hydroxide, while shaking with the magnetic stirrer, until the blue color formed disappeared, The rest of the metallic sodium was then added, cleaning off oil with filter paper. After the blue solution turned gray, shaking was continued for 30 minutes.

B. Preparation of DL-3-Hydroxy-3-Ethyl-3-Phenyl-Propionitrile (DL-HEPPN).

For 5 minutes, 14.035 gm (0.35 moles) acetonitrile dissolved in 200 ml ethyl ether was added to the sodamide solution previously prepared. After 30 minutes, the black solution was treated for 5 minutes with 49.2 grams (0.35 moles) propiophenone in 200 ml ether solution. After 5 minutes, the solution was poured into a suspension of 20 gm ammonium chloride in 200 ml ammonium hydroxide, and the mixture with stirred with a glass rod. Stirring with a magnetic shaker was continued for an hour. Ammonia was allowed to evaporate for 18 hours, and the solid residue was cooled in an ice bath, then pulverized with a glass rod. 50 ml of a cold HCL 3N solution was added, and the mixture was extracted with 100 ml ether. 25 ml of a hydrochloric acid solution was again added, and again extracted with 50 ml ether. Extractions with ether were continued until the solution came out clear (approx. 3 extractions).

The ether extracts with dried with anhydro-magnesium sulfate and distilled at a reduced pressure. Hydroxyethylphenyl propionitrile (HEPPN) distilled at 114°–115° C. at 0.5 mm. mercury. Yield was 29.3% and the fusion point was

52°0 C.

C. Preparation of DL-3-Hydroxy-3-Ethyl-3-Phenyl-Propionamide (DL-HEPP)

The above nitrile turns into the corresponding amide following Radziszewski's general method of alkaline hydrolysis. See, Kaiser et al., *J. Org. Chem.* 33, 3402 (1968) and Gowan et al., *Name of Organic Reactions*, p. 201 (1960). In a one liter, two opening matrass equipped with a magnetic shaker, refrigerant and a thermometer, there was added 18.85 gm (0.1 mole) of the above HEPPN, 41 ml of 30% hydrogen peroxide, 43 ml ethanol, and 3.2 ml of 6N sodium hydroxide. This mixture is exothermic and releases oxygen. When the temperature reached 50° C., the matrass was placed in an ice bath until temperature descended to 40° C. The temperature for this reaction should stay between 40 and 50° C. Approximately 30 min. later, heat evolution had stopped and the temperature was held at 50° C. by means of external heating with a heating cloth for 3 more hours.

While still warm, the mixture was carefully neutralized with a 5% sulfuric acid solution using litmus paper. Once neutralized, the mixture was extracted with 50 ml volumes of ethyl ether. The ether was distilled in a rotating evaporator, and the white solid residue was the DL-HEPP that crystallizes with water. DL-HEPP is soluble in ethyl alcohol, benzene and hot water, and insoluble in cold water. Its fusion point is 101°–102° C.

The yield obtained was 97.5%. DL-HEPP shows the following infrared maximums: 732 cm$^{-1}$ (—C$_6$H$_5$); 3042, 1452 and 1365 cm$^{-1}$ (—CH$_3$); 3419 cm$^{-1}$ (OH); 1163 cm$^{-1}$ (—C=0); 3 150 cm$^{-1}$ (—NH—); 1660 cm$^{-1}$ (—C=0); 872 and 503 cm$^{-1}$ (—C—C—); 3008 and 2936 cm$^{31\ 1}$ (—CH). Nuclear magnetic resonance spectrum shows the following maximums. $^1$H NMR (CDCL$_3$); ppm 0.77 (t,3H,CH$_3$) 1.88 q, 2H, —CH$_2$ Me); 2.73 (S,2H, —CH$_2$CO—); 4.6 (S, 1H,—OH); 5.88 (bs, 2H,—NH$_2$); 7.4 (m, 5H, H Phenyl).

EXAMPLE 3

Preparation of DL-4-Hydroxy-4-Ethyl-4-Phenyl-Butyramide (DL-HEPB)

The reaction was carried out in a matrass having three polished openings, equipped with a Hershberg shaker that extends through a cap equipped with a glass pipe and a rubber pipe and was closed airtight. The side opening was attached to a reflux condenser the end of which was connected a nitrogen source. The nitrogen source was attached to a mercury lock valve for regulating pressure. The third opening has a polished cap which opens to permit addition of the reactants. The device must be clean and air must be taken out. Once a vacuum was created, the vessel was filled with dry nitrogen, keeping the nitrogen flowing. The cap was opened and 3.6 gm (0.15 mole) sodium hydride (NaH) and 25 ml benzene are added, followed by the addition of 6.7 gm (0.05 mole) propiophenone and 26.13 gm (0.15 mole) diethyl succinate. Then, 25 ml more benzene was added.

To initiate the reaction, a small amount of ethanol (0.73 ml) was added, the vessel was covered and the nitrogen flow was stopped. The stirrer was then turned on, and hydrogen was produced. This hydrogen bubbles due to the mercury trap. Temperature was maintained below 40° C. After one hour, the reaction was almost finished. The mixture was then cooled with an ice bath, and 10.5 ml freezing acetic acid and water are added. The mixture was extracted with ether; the aqueous layer was washed once with ether and then discarded.

The combined ether solutions are repeatedly extracted with a 5% sodium carbonate solution until a sample of alkaline extract does not show apparent muddiness when acidified. The combined alkaline solutions acidify, and the oil formed was collected by extraction with ether. The ether solution was dried up with anhydrous sodium sulfate and evaporated under vacuum, leaving 11.4–11.6 g. (92–93% yield) of a semi-solid pale yellow color mixture. The raw product has an approximate equivalent weight of 261 (248 calculated) and can be used directly in the following steps of decarbetoxilation and lactonization.

The DL-γ-Ethyl-γ-Phenyl butyrolactone was then obtained as follows. 38 gm of the raw product of the preceding reaction was dissolved in 135 ml freezing acetic acid, 90 ml of 48% hydrobromic acid and 45 ml water and refluxed for 17 hours. The resulting solution was concentrated under vacuum, and the residue extracted with ether. The acid material was separated from ether solution by washing with a solution saturated with sodium bicarbonate. From this solution 14.73 gm of a partially crystalline material was obtained. This material was treated again with 68 ml acetic acid, 45 ml hydrobromic acid and 22 ml water and refluxed for 20 hours. It was then treated as mentioned above (vacuum concentration, extraction with ether, etc.) The acid material remaining from this treatment was a brown color gum of only 0.81 gm.

The neutral material ether solutions were washed with a saturated salt solution and then dried over sodium anhydride sulfate. Ether was discarded and the residue distilled, collecting a 160–165 or/7 mm fraction, which gives 22.41 gm (85% yield) lactone (DL-Ethyl,γ-phenyl-butyrolactone).

The obtained DL-γ-ethyl, γ-phenyl-butyrolactone was transformed into the hydroxamide as follows. 20 gm of the lactone with 60 ml ammonium hydroxide added thereto were placed in a 375 cm$^3$ autoclave and heated at 80°–90° C. for 2 hours, forming DL-4-hydroxy-4-ethyl-4-phenyl-butyramide. The raw product obtained this way had a fusion point of 109°–112° C. It recrystallized from alcohol/water in the form of white crystals with a fusion point of 113° C. It can also be recrystallized from propanol.

EXAMPLE 4

Anticonvulsant Activity

Male albino mice (NMR-1 strain) weighing 28–32 gm were used in a mouse anticonvulsant and rotarod test. Each of the test compounds (n=0, 1 and 2) were dissolved in a 10% polyethylene glycol-400 saline solution and were administered intraperitoneally (i.p.). Convulsant agents were dissolved in saline solution, buffered with 15 mmol/l Tris-HCl, pH 7.4, except for bicuculline, which was first dissolved in 0.025N HCl, adjusting to pH 4 with a 0.15 mol/l citrate-phosphate buffer. The convulsant dose inducing seizures in 97% of mice (CD$_{97}$) was determined and used in the pharmacological test. CD$_{97}$ values obtained were: 85 for pentetrazol (PTZ), 15 for 4-aminopyridine (4-AP), 3.3 for bicuculline (BIC), 20 for thiosemicarbazide (TSC), and 2.0 for strychnine (STR) expressed as mg kg$^{-1}$. The time of peak drug effect was evaluated for each anticonvulsant before determining the dose-response curves. Convulsant agents were either injected subcutaneously (s.c. into the back of the neck (BIC, picrotoxin (PIC) and PTZ) or administered i.p. (4-AP, TSC and STR).

Abolition of the tonic components of the seizure was the end point, except for PTZ, where suppression of seizures of at least 5 seconds duration was considered the end point. The vehicle was inactive in all the test procedures. The ED$_{50}$, TD$_{50}$ and 95% confidence intervals were calculated by the method of Litchfield and Wilcoxon. See Litchfield et al., *J.*

Pharmacol. Exp. Ther. 96, 99 (1949).

In a maximal electroshock test, maximal seizures were induced by application of an electrical current across the brain via carclip electrodes. The stimulus parameters for mice were 30–35 mA, A.C. in pulses of 60 Hz for 200 ms. Each compound was tested at the time of peak drug effect. The dose at which the hind limb tonic seizure was blocked in 50% of the animals ($ED_{50}$ value) was determined by probit analysis.

EXAMPLE 5

Neurotoxic Effects

In a rotarod test, separate groups of mice were trained to stay on an accelerating rotarod that rotated initially at 2.16 rpm, then increased in speed to reach 22.5 rpm in 4 min. The drum diameter was 2.8 cm. Trained animals were dosed with the test compound or drug vehicle and were tested at the time of peak drug effect to measure the effects of the drug on motor performance. The dose at which 50% of the animals fell off the rotarod ($TD_{50}$ value) was determined by probit analysis.

The results for Examples 5 and 6 are set forth in the following table:

| Cmpd. | n | Time of test (min) post dosing[c] | Pharmacological test[a] $ED_{50}$ (mg kg$^{-1}$) | | | | | | | $TD_{50}$ (mg kg$^{-1}$) Rotarod ataxia[b] |
|---|---|---|---|---|---|---|---|---|---|---|
| | | | MES | PTZ | 4-AP | BIC | TSC | STR | PIC | |
| (±) 1 | 0 | 30[d] | 126 (119–133)[f] | 67 (68–77) | 24 (13–43) | 29 (17–50) | 47 (24–92) | 56 (30–102) | e) | 132 (119–146) |
| (±) 2 | 1 | 10[g] | 144 (139–149) | 63 (56–72) | 19 (10–35) | 38 (25–88) | 43 (23–80) | h) | i) | 214 (203–226) |
| (±) 53A | 2 | 30[j] | 148 (138–158) | 63 (56–71) | 29 (16–51) | 30 (18–50) | 73 (40–131) | 106 (54–210) | e) | 111 (100–122) |
| (±) 3B NIH[m] | 2 | 30 | 147 (126–172) | 58 (43–79) | k) | k) | k) | k) | k) | 168[l] (137–206) |

[a]Seizures provoked by: maximal electroshock (MES), pentetrazol (PTZ), 4-aminopyridine (4-AP), bicuculline (BIC), thiosemicarbazide (TSC), strychnine (STR) and picrotoxin (PIC).
[b]Accelerating rotarod.
[c]To peak drug effect.
[d]TSC and PTZ were administered 10 min post-dosing.
[e]No effects at 80 mgkg$^{-1}$ for 1 or at 120 mgkg$^{-1}$ for 3 were observed.
[f]95% confidence interval.
[g]STR and PIC were administered 15 min post-dosing and the rotarod ataxia test was made 30 min post-dosing.
[h]Maximum 30% protection at 100 mgkg$^{-1}$.
[i]Maximum 37% protection at 130 mgkg$^{-1}$.
[j]PTZ was administered 10 min post-dosing.
[k]Not tested.
[l]Constant speed rotarod was used.
[m]Data obtained from NIH through the ADD program (registr. no. for 3B is 41029; See, Gladding, ADD Program Epilepsy Branch, NINCDS, NIH Bethesda, MD, USA (1978).

It will be understood that the foregoing description is of preferred exemplary embodiments of the invention, and that the invention is not limited to the specific forms shown. For example, various derivatives of the compounds illustrated can be made by the methods described. These and other modifications may be made in the invention without departing from the scope of the invention as expressed in the appended claims.

We claim:
1. (±)-3-hydroxy-3-phenylpentamide.

* * * * *